US011786675B2

(12) United States Patent
Liu

(10) Patent No.: US 11,786,675 B2
(45) Date of Patent: Oct. 17, 2023

(54) INHALER AND ATOMIZATION COMPONENT THEREOF

(71) Applicant: Shenzhen Smoore Technology Limited, Guangdong (CN)

(72) Inventor: Pingkun Liu, Guangdong (CN)

(73) Assignee: Shenzhen Smoore Technology Limited, Shenzhen (CN)

( * ) Notice: Subject to any disclaimer, the term of this patent is extended or adjusted under 35 U.S.C. 154(b) by 517 days.

(21) Appl. No.: 16/987,842

(22) Filed: Aug. 7, 2020

(65) Prior Publication Data
US 2020/0359692 A1 Nov. 19, 2020

Related U.S. Application Data

(63) Continuation of application No. 15/566,242, filed as application No. PCT/CN2015/077667 on Apr. 28, 2015, now Pat. No. 10,772,353.

(51) Int. Cl.
*A61M 11/04* (2006.01)
*H05B 3/04* (2006.01)
(Continued)

(52) U.S. Cl.
CPC .......... *A61M 11/042* (2014.02); *A24F 40/42* (2020.01); *A24F 40/48* (2020.01); *A24F 40/485* (2020.01);
(Continued)

(58) Field of Classification Search
CPC ............... A61M 11/042; A61M 15/06; A61M 2205/3653; A61M 2205/3673;
(Continued)

(56) References Cited

U.S. PATENT DOCUMENTS

| 2014/0150785 A1* | 6/2014 | Malik .................. A61M 11/042 |
| | | 128/202.21 |
| 2014/0261490 A1 | 9/2014 | Kane |

(Continued)

FOREIGN PATENT DOCUMENTS

| CN | 103380952 A | 11/2013 |
| CN | 203457802 U | 3/2014 |

(Continued)

OTHER PUBLICATIONS

CN Office Action dated Mar. 27, 2017 in re CN Application No. 201510209717.1.

(Continued)

*Primary Examiner* — Kendra D Carter
*Assistant Examiner* — Arielle Wolff
(74) *Attorney, Agent, or Firm* — COATS & BENNETT, PLLC

(57) ABSTRACT

An atomization assembly of an inhaler includes: a liquid reservoir defining a main liquid storage chamber therein for storing liquid and an auxiliary liquid storage chamber, the liquid reservoir further defining a liquid-draining aperture between the main liquid storage chamber and the auxiliary liquid storage chamber; an atomizing core connected to the liquid reservoir; and a movable member configured to move back and forth between a first position towards the liquid-draining aperture and a second position away from the liquid-draining aperture, wherein when the movable member is in the first position, the movable member seals the liquid-draining aperture, such that the main liquid storage chamber is isolated from the auxiliary liquid storage chamber; when the movable member is in the second position, the movable member is separated from the liquid-draining aperture, thereby communicating the main liquid storage chamber with the auxiliary liquid storage chamber.

17 Claims, 13 Drawing Sheets

(51) Int. Cl.
    *A24F 40/48*         (2020.01)
    *A24F 40/42*         (2020.01)
    *A24F 40/485*       (2020.01)
    *A61M 15/06*        (2006.01)
    *H05B 3/44*          (2006.01)
    *A24F 40/10*        (2020.01)

(52) U.S. Cl.
    CPC ............... *A61M 15/06* (2013.01); *H05B 3/04*
    (2013.01); *H05B 3/44* (2013.01); *A24F 40/10*
    (2020.01); *A61M 2205/3653* (2013.01); *A61M*
    *2205/3673* (2013.01); *A61M 2205/8206*
    (2013.01); *H05B 2203/014* (2013.01); *H05B*
    *2203/021* (2013.01); *H05B 2203/022* (2013.01)

(58) Field of Classification Search
    CPC . A61M 2205/8206; A24F 40/42; A24F 40/48;
    A24F 40/485; A24F 40/10; H05B 3/04;
    H05B 3/44; H05B 2203/014; H05B
    2203/021; H05B 2203/022

See application file for complete search history.

(56) References Cited

U.S. PATENT DOCUMENTS

2015/0216232 A1*   8/2015   Bless ..................... A24F 40/70
                                                                             285/344
2017/0295847 A1*  10/2017   Liu ......................... F22B 1/284

FOREIGN PATENT DOCUMENTS

| CN | 203633506 U | 6/2014 | |
|---|---|---|---|
| CN | 203828081 U | 9/2014 | |
| CN | 204444260 U | 7/2015 | |
| CN | 204444261 U | 7/2015 | |
| CN | 104824846 A | 8/2015 | |
| CN | 104839893 A | 8/2015 | |
| CN | 204796738 U | 11/2015 | |
| WO | 2014150229 A1 | 9/2014 | |
| WO | WO-2016149932 A1 * | 9/2016 | ............. A24F 47/00 |

OTHER PUBLICATIONS

CN Office Action dated Dec. 8, 2017 in re CN Application No. 201510209717.1.
CN Search Report in re CN Application No. 201510209717.1.
International Search Report and Written Opinion dated Jan. 20, 2016 in re International Application No. PCT/CN2015/077667 filed Apr. 28, 2015.

* cited by examiner

INHALER AND ATOMIZATION COMPONENT THEREOF

CROSS-REFERENCE TO RELATED APPLICATIONS

This application is a continuation application of U.S. patent application Ser. No. 15/566,242, filed Oct. 13, 2017, entitled, "INHALER AND ATOMIZATION COMPONENT THEREOF", which is a national stage application under 35 U.S.C. 371 of PCT Application No. PCT/CN2015/077667 having an international filing date of Apr. 28, 2015, the contents of which are incorporated by reference herein in their entirety for all purposes.

FIELD OF THE INVENTION

The present disclosure relates to a field of an equipment for delivering atomizing medium into human body, and more particularly relates to an inhaler and an atomizing assembly thereof.

BACKGROUND OF THE INVENTION

Inhaler is an equipment for delivering atomizing medium into the human body, it mainly includes an electronic cigarette for substituting cigarette and a medical aerosol inhaler for treating upper respiratory diseases.

In a conventional electronic cigarette and a medical aerosol inhaler with a similar structure, a liquid storage chamber thereof is in direct communication with a wick, and the wick is connected to the outside environment through a mouthpiece. When the electronic cigarette is placed for a long time without use, volatile substances such as nicotine in the wick will gradually evaporate to the outside environment from the mouthpiece, thus drawing the liquid constantly from the liquid storage chamber, which will eventually result in deterioration of the taste of electronic cigarette placed for a long time. Similarly, with respect to the medical aerosol inhaler with the similar structure, the liquid medicine thereof often has volatile substances, and the problem of the reduced efficacy due to the long time placement still occurs.

SUMMARY OF THE INVENTION

Accordingly, it is necessary to provide an inhaler and an atomizing assembly thereof, which can address the problem of volatilizing of the liquid in the liquid storage chamber.

An atomization assembly of an inhaler is configured to be detachably connected to a battery assembly of the inhaler, the atomization assembly includes a liquid reservoir, an atomizing core, and a movable member.

The liquid reservoir defines a liquid storage chamber therein for storing liquid.

The atomizing core is fixed to the liquid reservoir, the atomizing core includes a wick.

The movable member is movably connected to the liquid reservoir, when the atomization assembly is not connected to the battery assembly, the movable member seals the liquid reservoir, such that the liquid in the liquid reservoir is isolated from the wick; when the atomization assembly is connected to the battery assembly, the movable member moves towards the battery assembly, thereby communicating the liquid storage chamber with the wick.

In one embodiment, the liquid reservoir includes an inner tube, an outer tube, and a liquid guide piece, the inner tube defines an air flow channel therein, the liquid storage chamber is formed between the inner tube and the outer tube; the liquid guide piece is located between the inner tube and the outer tube, and is located at an opening of the liquid storage chamber; the liquid guide piece defines a liquid-draining aperture thereon, one end of the liquid-draining aperture is in communication with the liquid storage chamber; when the atomization assembly is not connected to the battery assembly, the movable member seals the other end of the liquid-draining aperture; when the atomization assembly is connected to the battery assembly, the movable member moves towards the battery assembly, such that the other end of the liquid-draining aperture is in communication with the wick.

In one embodiment, the atomizing core further includes:

an atomizing base defining an atomizing chamber and a liquid absorbing opening, the wick is at least partially located inside the atomizing chamber, the wick is in contact with the liquid in the liquid storage chamber via the liquid absorbing opening; and an atomizing cover located on the atomizing base, the atomizing cover extends at least partially into an inside of the inner tube, and the atomizing cover defines a communication aperture communicating the atomizing chamber and the air flow channel.

In one embodiment, at least part of the movable member is made of a magnetic material, the movable member is capable of being attracted by a magnet in the battery assembly to move towards the battery assembly;

wherein the atomization assembly of the inhaler further comprises an elastic member, one end of the elastic member is connected to the movable member, the other end of the elastic member is connected to the liquid reservoir, a direction of urging the movable member by the elastic member is opposite to a moving direction of the movable member when the movable member moves towards the battery assembly.

In one embodiment, the movable member includes:

a main body shaped as a barrel, the main body being movably sleeved on the atomizing base;

a sealing member located at an end of the main body proximately to the liquid guide piece, the sealing member being aligned with the liquid-draining aperture; and a ferric member located at an end of the main body proximately to the battery assembly.

In one embodiment, the movable member is provided with a first thread engaging with a second thread on the battery assembly, the battery assembly rotatably drives the movable member to move.

In one embodiment, the atomization assembly further includes an elastic member, one end of the elastic member is connected to the movable member, the other end of the elastic member is connected to the liquid reservoir, a direction of urging the movable member by the elastic member is opposite to a moving direction of the movable member when the movable member moves towards the battery assembly.

In one embodiment, the movable member includes:

a main body shaped as a barrel, the main body being movably sleeved on the atomizing base;

a sealing member located at an end of the main body proximately to the liquid guide piece, the sealing member being aligned with the liquid-draining aperture;

wherein the first thread is an external thread located at one end of the main body proximately to the battery assembly.

In one embodiment, the movable member includes:

a main body shaped as a barrel, the main body being movably sleeved on the atomizing base;

a sealing member located at an end of the main body proximately to the liquid guide piece, the sealing member being aligned with the liquid-draining aperture; and a ferric member located at an end of the main body proximately to the battery assembly.

In one embodiment, the movable member is provided with a first thread engaging with a second thread on the battery assembly, the battery assembly rotatably drives the movable member to move.

In one embodiment, the atomization assembly further includes an elastic member, one end of the elastic member is connected to the movable member, the other end of the elastic member is connected to the liquid reservoir, a direction of urging the movable member by the elastic member is opposite to a moving direction of the movable member when the movable member moves towards the battery assembly.

In one embodiment, the movable member includes:

a main body shaped as a barrel, the main body being movably sleeved on the atomizing base;

a sealing member located at an end of the main body proximately to the liquid guide piece, the sealing member being aligned with the liquid-draining aperture;

wherein the first thread is an external thread located at one end of the main body proximately to the battery assembly.

In one embodiment, the sealing member is located inside the outer tube, the movable member further comprises a first sealing ring disposed on the sealing member, the first sealing ring is located between the sealing member and the outer tube.

In one embodiment, the atomizing core includes a second sealing ring, the atomizing base defines an annular groove on an outer wall thereof, the second sealing ring is at least partially embedded in the annular groove, thereby sealing a gap between the main body and the atomizing base.

In one embodiment, the liquid reservoir further includes:

a support base having an annular shape and located on an opening of the outer tube, wherein the main body extends through the support base, an end of the elastic member abuts the support base; and a stop ring located between the outer tube and the atomizing base, wherein the stop ring is fixed to the support base, and the elastic member is located between the stop ring and the main body.

In one embodiment, the liquid reservoir further includes a positioning portion located on the support base, the positioning portion protrudes from an inner side of the support base, the sidewall of the main body has a notch extending in an axial direction thereof, the positioning portion is engaged in the notch to restrict the main body from rotating.

An inhaler includes the atomization assembly of the inhaler and a battery assembly, wherein the atomizing assembly of the inhaler is detachably connected to a battery assembly.

According to the foregoing inhaler and the atomization assembly thereof, the atomizing core is fixed to the liquid reservoir, and the movable member is movably connected to the liquid reservoir. When the atomization assembly is not connected to the battery assembly, the movable member seals the liquid reservoir, such that the liquid in the liquid reservoir is isolated from the wick, thus avoiding the liquid in the liquid storage chamber from being absorbed and volatilized by the wick. When the atomization assembly is connected to the battery assembly, the movable member moves towards the battery assembly, such that the liquid storage chamber is in communication with the wick, and the wick can absorb liquid for atomizing. When the inhaler is not used for a long period of time, the atomization assembly can be separated from the battery assembly, such that the movable member can seal the liquid reservoir and prevent the liquid in the liquid storage chamber from being volatilized.

DETAILED DESCRIPTION OF THE EMBODIMENTS

Reference will now be made to the drawings to describe, in detail, embodiments of the present inhaler and atomization assembly thereof. The various embodiments of the invention may, however, be embodied in many different forms and should not be construed as limited to the embodiments set forth herein. Rather, these embodiments are provided so that this disclosure will be thorough and complete, and will fully convey the scope of the invention to those skilled in the art.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Figure 1:
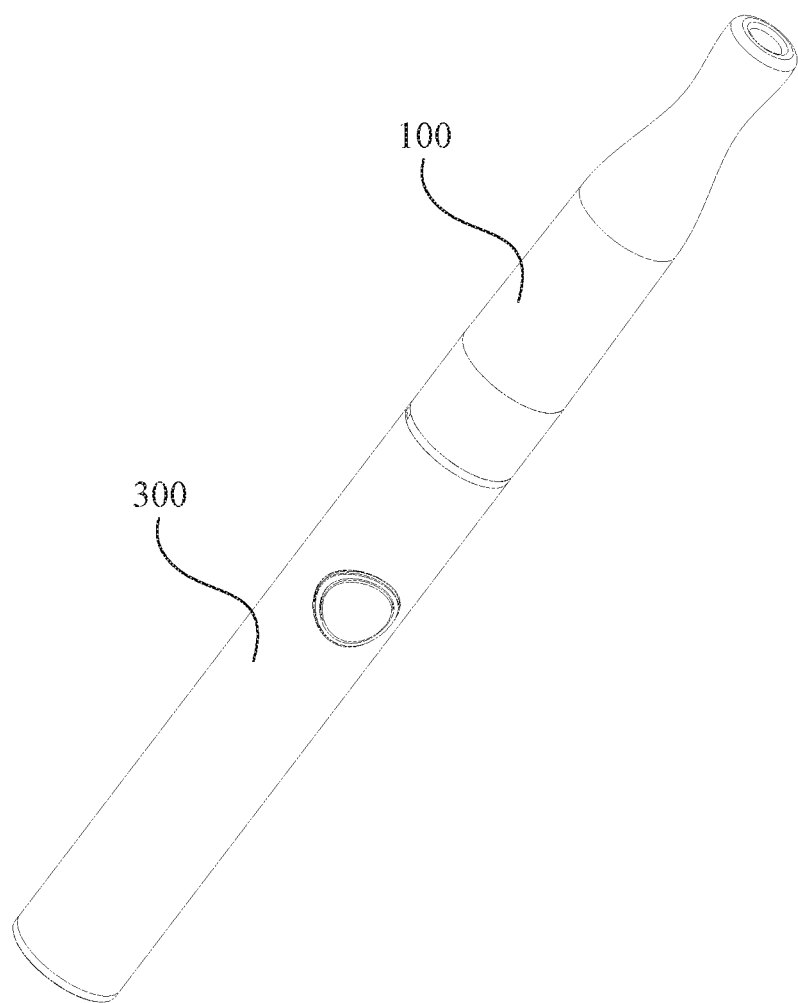
FIG. 1 is a perspective view of an inhaler according to one embodiment.

Referring to FIG. 1, an inhaler 10 according to one embodiment includes an atomization assembly 100 and a battery assembly 300. The inhaler 10 of the present embodiment can be used to atomize liquid and deliver the atomized vapor into the human body. The inhaler 10 can be an electronic cigarette, or a medical aerosol inhaler and so on.

Figure 2:
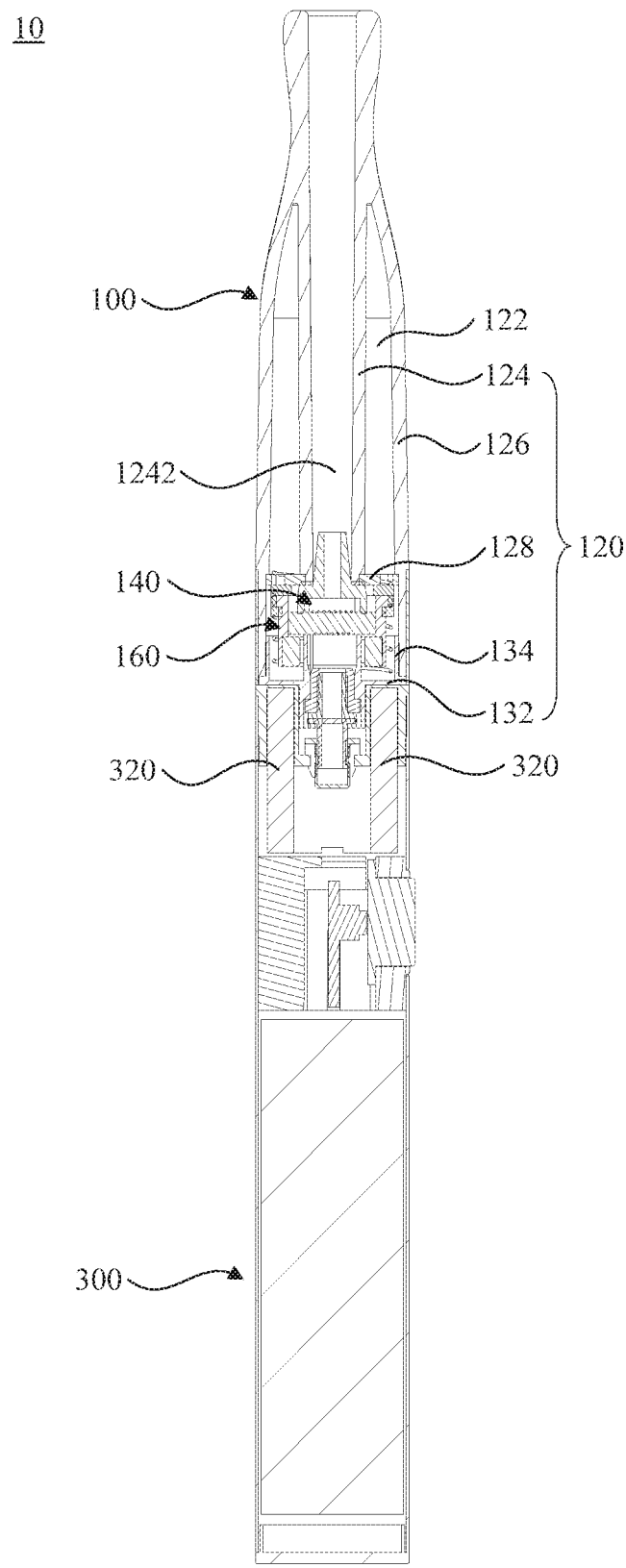
FIG. 2 is a cross-sectional view of the inhaler of FIG. 1.
Figure 3:
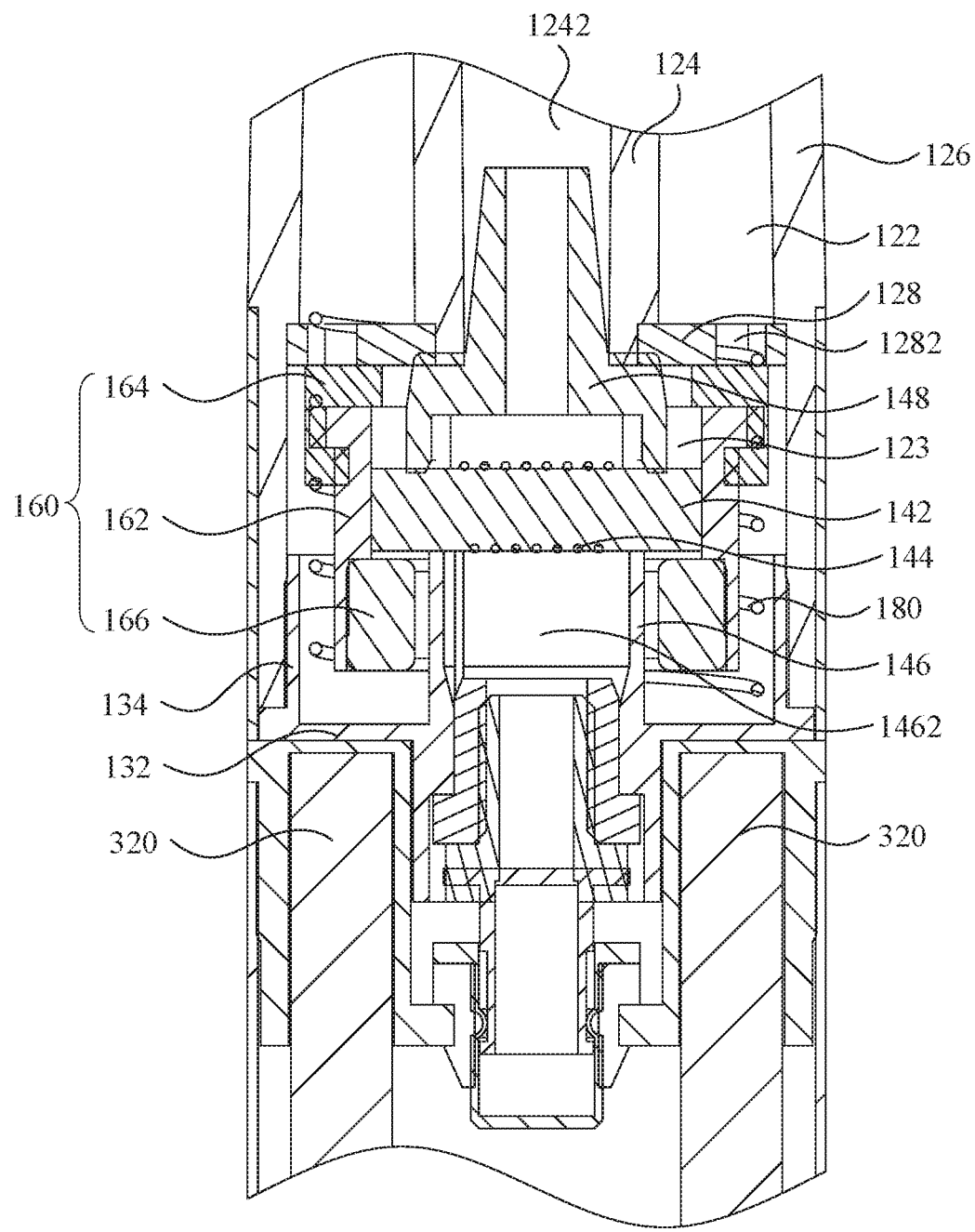
FIG. 3 is an enlarged view of the inhaler of FIG. 2.

Referring to FIG. 2 and FIG. 3, the atomization assembly 100 according to one embodiment includes a liquid reservoir 120, an atomizing core 140, and a movable member 160. The liquid reservoir 120 defines a main liquid storage chamber 122 therein. When the inhaler 10 is an electronic cigarette, the liquid stored in the liquid storage chamber 122 can be tobacco liquid; when the inhaler 10 is a medical aerosol inhaler, the liquid stored in the main liquid storage chamber 122 can be a liquid medicine. The liquid reservoir 120 further defines an auxiliary liquid storage chamber 123 adjacent to the main liquid storage chamber 122, and a liquid-draining aperture 1282 between the main liquid storage chamber 122 and the auxiliary liquid storage chamber 123.

The atomizing core 140 is fixed to the liquid reservoir 120. In the illustrated embodiment, the atomizing core 140 is located in the auxiliary liquid storage chamber 123. The atomizing core 140 includes a wick 142. The wick 142 can be wound by a heating wire 144. The liquid adsorbed in the wick 142 is heated by the heating wire 144 to achieve atomization. The movable member 160 is movably connected to the liquid reservoir 120. When the atomization assembly 100 is not connected to the battery assembly 300, the movable member 160 seals the liquid reservoir 120, such that the main liquid reservoir 122 is isolated from the auxiliary liquid storage chamber 123, and the liquid in the main liquid reservoir 122 cannot flow into the auxiliary liquid storage chamber 123 to reach the wick 142. When the atomization assembly 100 is connected to the battery assembly 300, the movable member 160 moves towards the battery assembly 300, thereby communicating the main liquid storage chamber 122 with the auxiliary liquid storage chamber 123.

In the illustrated embodiment, the atomizing core 140 is fixed to the liquid reservoir 120, and the movable member 160 is movably connected to the liquid reservoir 120. When the atomization assembly 100 is not connected to the battery assembly 300, the movable member 160 seals the main liquid reservoir 122, such that the liquid in the main liquid reservoir 122 is isolated from the wick 142, thus avoiding the liquid in the main liquid storage chamber 122 from being absorbed and volatilized by the wick 142. When the atomization assembly 100 is connected to the battery assembly 300, the movable member 160 moves towards the battery assembly 300, such that the main liquid storage chamber 122 is in communication with the auxiliary liquid storage chamber 123, and the wick 142 can absorb liquid from the auxiliary liquid storage chamber 123 for atomizing. When the inhaler 10 is not used for a long period of time, the atomization assembly 100 can be separated from the battery assembly 300, such that the movable member 160 can seal the liquid reservoir 120 and prevent the liquid in the main liquid storage chamber 122 from being volatilized.

In alternative embodiment, the liquid reservoir 120 can include an inner tube 124, an outer tube 126, and a liquid guide piece 128. The inner tube 124 defines an air flow channel 1242 therein. The main liquid storage chamber 122 is formed between the inner tube 124 and the outer tube 126. The liquid guide piece 128 is located between the inner tube 124 and the outer tube 126, and the liquid guide piece 128 is located at an opening of the liquid storage chamber 122. The liquid guide piece 128 defines a liquid-draining aperture 1282 thereon. One end of the liquid-draining aperture 1282 is in communication with the main liquid storage chamber 122, the other end of the liquid-draining aperture 1282 is in communication with the auxiliary liquid storage chamber 123. When the atomization assembly 100 is not connected to the battery assembly 300, the movable member 160 seals the other end of the liquid-draining aperture 1282. When the atomization assembly 100 is connected to the battery assembly 300, the movable member 160 moves towards the battery assembly 300, such that the other end of the liquid-draining aperture 1282, such that the main liquid storage chamber 122 is in communication with the auxiliary liquid storage chamber 123, and the liquid from the main liquid storage chamber 122 can flow into the auxiliary liquid storage chamber 123 via the liquid-draining aperture 1282. Since the liquid flows out through the liquid-draining aperture 1282, the flow rate can be reduced, and the amount of the liquid outflow can be easily controlled.

Figure 4:
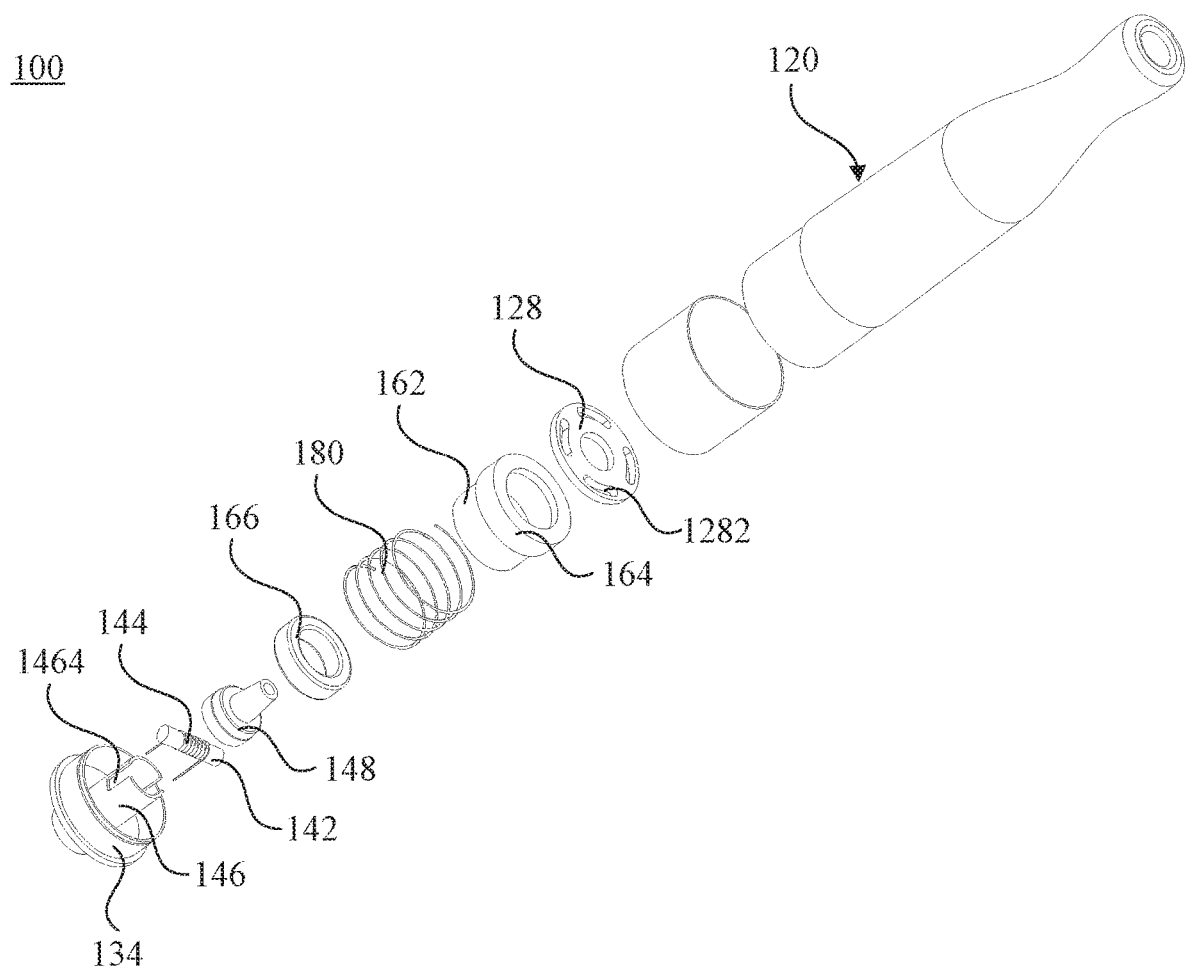
FIG. 4 is an exploded view of an atomizing assembly of the inhaler of FIG. 1.

Referring to FIG. 4, in one embodiment, the atomizing core 140 can further includes an atomizing base 146 and an atomizing cover 148. The atomizing base 146 defines an atomizing chamber 1462 and a liquid absorbing opening 1464. The wick 142 is at least partially located inside the atomizing chamber 1462. The wick 142 is in contact with the liquid in the auxiliary liquid storage chamber 123 via the liquid absorbing opening 1464. The atomizing cover 148 is located on the atomizing base 146. The atomizing cover 148 extends at least partially into an inside of the inner tube 124. The atomizing cover 148 defines a communication aperture communicating the atomizing chamber 1462 and the air flow channel 1242. The atomization cover 148 can be resilient to seal a gap between the inner tube 124 and the atomization core 140. Meanwhile, the atomization cover 148 can cushion the pressure applied to the inner tube 124 by the atomizing core 140 during the assembly of the battery assembly 300, thus increasing the reliability of the structure.

In addition, in the illustrated embodiment, at least part of the movable member 160 is made of a magnetic material. The battery assembly 300 includes a magnet 320. The movable member 160 can be attracted by the magnet 320 of the battery assembly 300 to move towards the battery assembly 300. The atomization assembly 100 of the inhaler 10 further includes an elastic member 180. One end of the elastic member 180 is connected to the movable member 160, the other end of the elastic member 180 is connected to the liquid reservoir 120. A direction of force applied to the movable member 160 by the elastic member 180 is opposite to a moving direction of the movable member 160 when the movable member 160 moves towards the battery assembly 300.

The magnet 320 of the battery assembly 300 can be a permanent magnet, or an electromagnet controlled by a switch. When the magnet 320 is an electromagnet, the movable member 160 can be controlled by a switch of the battery assembly 300. The switch can be a switch which can control operating of the heating wire 144, or may be a separate switch. When the atomization assembly 100 is connected to the battery assembly 300, the magnet 320 will attract the movable member 160, such that the movable member 160 moves towards the atomization assembly 100 and opens the liquid-draining aperture 1282. The elastic member 180 can be a spring, a rubber tube, a rubber pad, or a set of resilient sheet. In the illustrated embodiment, the elastic member 180 is a pressed spring. When the atomization assembly 100 is separated from the battery assembly 300, the elastic member 180 applies a reverse force to the movable member 160 to seal the liquid-draining aperture 1282.

Figure 5:
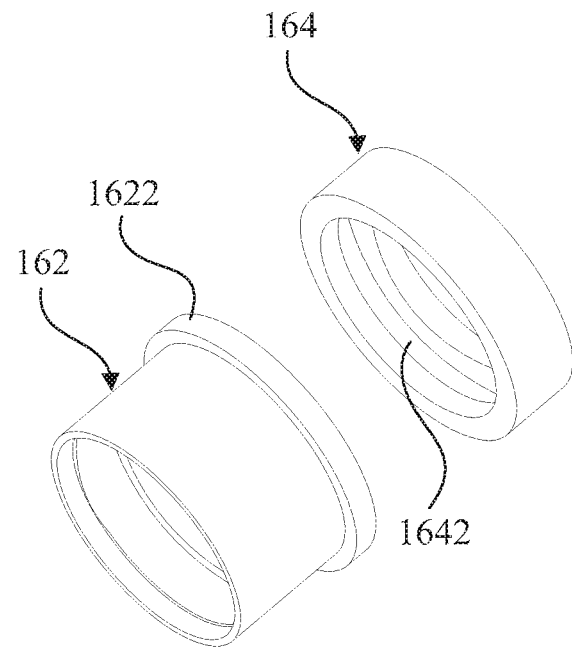
FIG. 5 is a schematic view of a main body and a sealing member of the inhaler of FIG. 1.

In one embodiment, the movable member 160 includes a main body 162, a sealing member 164, and a ferric member 166. The main body 162 is shaped as a barrel and is movably sleeved on the atomizing base 146. The main body 162 can be made of metal or plastic. The sealing member 164 is located at an end of the main body 162 proximately to the liquid guide piece 128, and the sealing member is aligned with the liquid-draining aperture 1282. The sealing member 164 can be made of an elastic material such as silica gel. The configuration of the sealing member 164 can improve the sealing effect of the movable member 160 to the liquid-draining aperture 1282 when the atomization assembly 100 is not connected to the battery assembly 300. Referring also to FIG. 5, the sealing member 164 defines an embedding groove 1642 on an inner side thereof, and the main body 162 is provided with a protruding ring 1622. The protruding ring 1622 is embedded in the embedding groove 1642, such that the main body 162 is firmly connected to the sealing member 164. In one embodiment, the elastic member 180 is sleeved on the main body 162, and the end of the elastic member 180 abuts the sealing member 164.

The ferric member 166 is located at an end of the main body 162 proximately to the battery assembly 300. The configuration of the ferric member 166 can increase the attraction of the atomization assembly 100 to the movable member 160. The end of the main body 162 proximately to the battery assembly 300 may define a receiving groove, the ferric member 166 can be an annular iron piece, which is riveted into the receiving groove by riveting.

Figure 6:
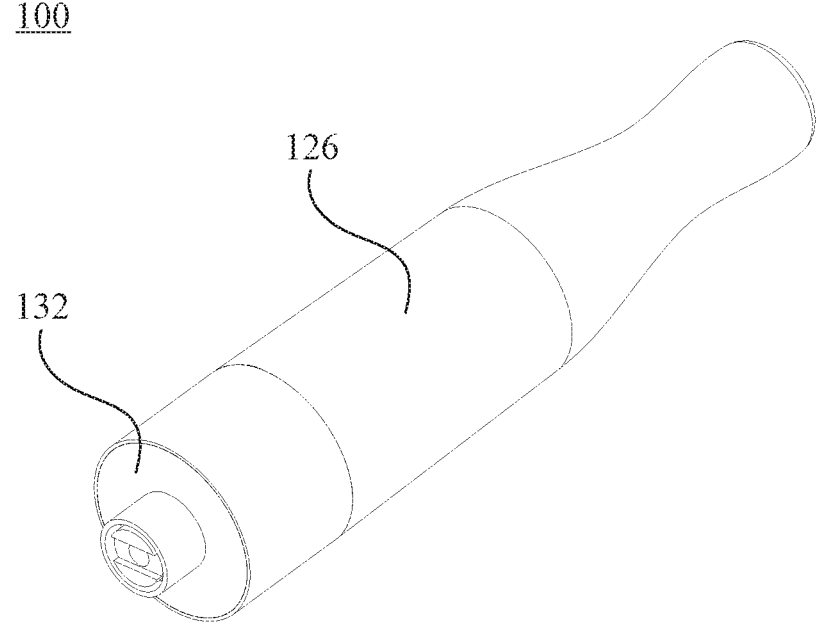
FIG. 6 is a perspective view of the atomizing assembly of the inhaler of FIG. 1.

Referring also to FIG. 6, in one embodiment, the liquid reservoir 120 further includes a support base 132 and a stop ring 134. The support base 132 has an annular shape and is located on an opening of the outer tube 126. The support base 132 is fixed to the outer tube 126. The main body 162 extends through the support base 132. The elastic member 180 has an end abutting the support base 132. The stop ring 134 is located between the outer tube 126 and the atomizing base 146. The stop ring 134 is fixed to the support base 132. In one embodiment, the stop ring 134 and the support base 132 can be integrally formed. The elastic member 180 is located between the stop ring 134 and the main body 162. When the elastic member 180 moves in a gap between the stop ring 134 and the main body 162, the movement of the elastic member 180 can be guided by the stop ring 134 and the main body 162. Meanwhile, the stop ring can restrict the movement of the movable member 160, so as to determine the distance by which the movable member 160 is moved when the battery assembly 300 is assembled.

Figure 7:
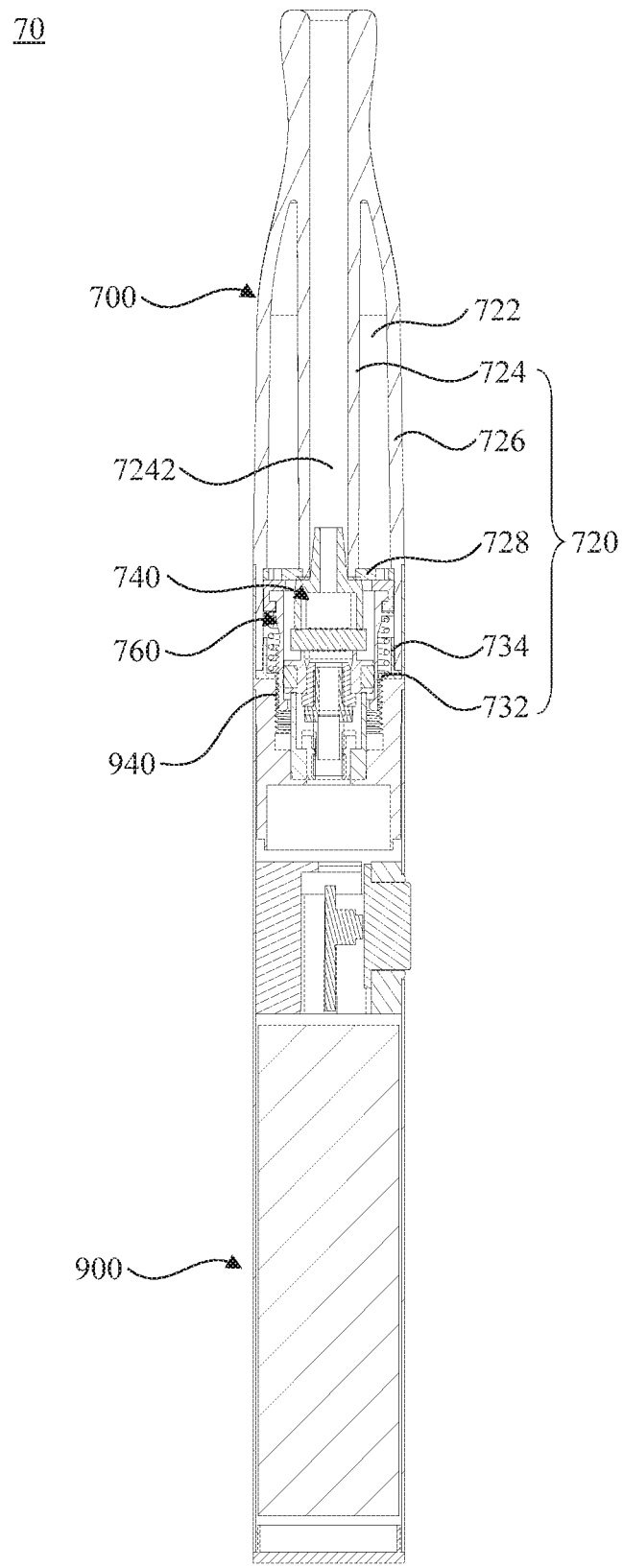
FIG. 7 is a cross-sectional view of an inhaler according to another embodiment.

Referring to FIG. 7, an inhaler 70 according to another embodiment includes an atomization assembly 700 and a battery assembly 900. The inhaler 70 of the present embodiment can be used to atomize liquid and deliver the atomized vapor into the human body. The inhaler 10 can be an electronic cigarette, or a medical aerosol inhaler and so on.

Figure 8:
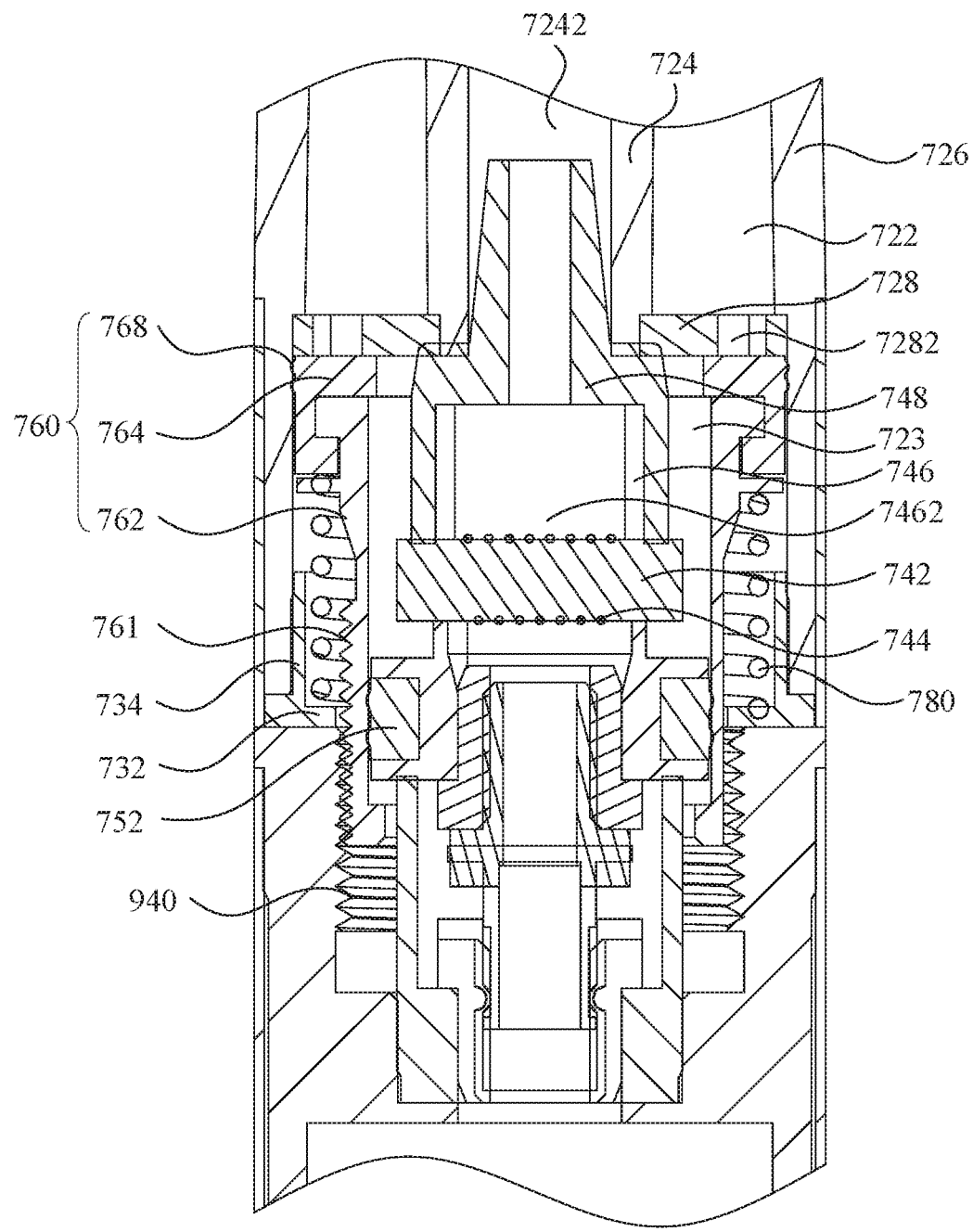
FIG. 8 is an enlarged view of the inhaler of FIG. 7.

Referring to FIG. 8, the atomization assembly 700 according to one embodiment includes a liquid reservoir 720, an atomizing core 740, and a movable member 760. The liquid reservoir 720 defines a main liquid storage chamber 722 therein. When the inhaler is an electronic cigarette, the liquid stored in the main liquid storage chamber 722 can be tobacco liquid; when the inhaler is a medical aerosol inhaler, the liquid stored in the main liquid storage chamber 722 can be a liquid medicine. The liquid reservoir 720 further defines an auxiliary liquid storage chamber 723 adjacent to the main liquid storage chamber 722, and a liquid-draining aperture 7282 between the main liquid storage chamber 722 and the auxiliary liquid storage chamber 723.

The atomizing core 740 is fixed to the liquid reservoir 720. In the illustrated embodiment, the atomizing core 740 is located in the auxiliary liquid storage chamber 723. The atomizing core 740 includes a wick 742. The wick 742 can be wound by a heating wire 744. The wick 742 can absorb the liquid in the auxiliary liquid storage chamber 723, and the liquid adsorbed in the wick 742 is heated by the heating wire 744 to achieve atomization. The movable member 760 is movably connected to the liquid reservoir 720. When the atomization assembly 700 is not connected to the battery assembly 900, the movable member 760 seals the liquid reservoir 720, such that the main liquid reservoir 722 is isolated from the auxiliary liquid storage chamber 723, and the liquid in the main liquid reservoir 722 cannot flow into the auxiliary liquid storage chamber 723 to reach the wick 742. When the atomization assembly 700 is connected to the battery assembly 900, the movable member 760 moves towards the battery assembly 900, thereby communicating the main liquid storage chamber 722 with the with the auxiliary liquid storage chamber 723.

In the illustrated embodiment, the atomizing core 740 is fixed to the liquid reservoir 720, and the movable member 760 is movably connected to the liquid reservoir 720. When the atomization assembly 700 is not connected to the battery assembly 900, the movable member 760 seals the main liquid reservoir 722, such that the liquid in the main liquid reservoir 722 is isolated from the wick 742, thus avoiding the liquid in the main liquid storage chamber 722 from being absorbed and volatilized by the wick 742. When the atomization assembly 700 is connected to the battery assembly 900, the movable member 760 moves towards the battery assembly 900, such that the main liquid storage chamber 722 is in communication with the auxiliary liquid storage chamber 723, and the wick 742 can absorb liquid for atomizing. When the inhaler 70 is not used for a long period of time, the atomization assembly 700 can be separated from the battery assembly 900, such that the movable member 760 can seal the main liquid storage chamber 722 and prevent the liquid in the main liquid storage chamber 722 from being volatilized.

In one embodiment, the liquid reservoir 720 can include an inner tube 724, an outer tube 726, and a liquid guide piece 728. The inner tube 724 defines an air flow channel 7242 therein. The liquid storage chamber 722 is formed between the inner tube 724 and the outer tube 726. The liquid guide piece 728 is located between the inner tube 724 and the outer tube 726, and the liquid guide piece 728 is located at an opening of the main liquid storage chamber 722. The liquid guide piece 728 defines a liquid-draining aperture 7282 thereon. One end of the liquid-draining aperture 7282 is in communication with the main liquid storage chamber 722, the other end of the liquid-draining aperture 7282 is in communication with the auxiliary liquid storage chamber 723. When the atomization assembly 700 is not connected to the battery assembly 900, the movable member 760 seals the other end of the liquid-draining aperture 7282. When the atomization assembly 700 is connected to the battery assembly 900, the movable member 760 moves towards the battery assembly 900, such that the other end of the liquid-draining aperture 7282, such that the main liquid storage chamber 722 is in communication with the auxiliary liquid storage chamber 723, and the liquid from the main liquid storage chamber 722 can flow into the auxiliary liquid storage chamber 723 via the liquid-draining aperture 7282. Since the liquid flows out through the liquid-draining aperture 7282, the flow rate can be reduced, and the amount of the liquid outflow can be easily controlled.

Figure 9:
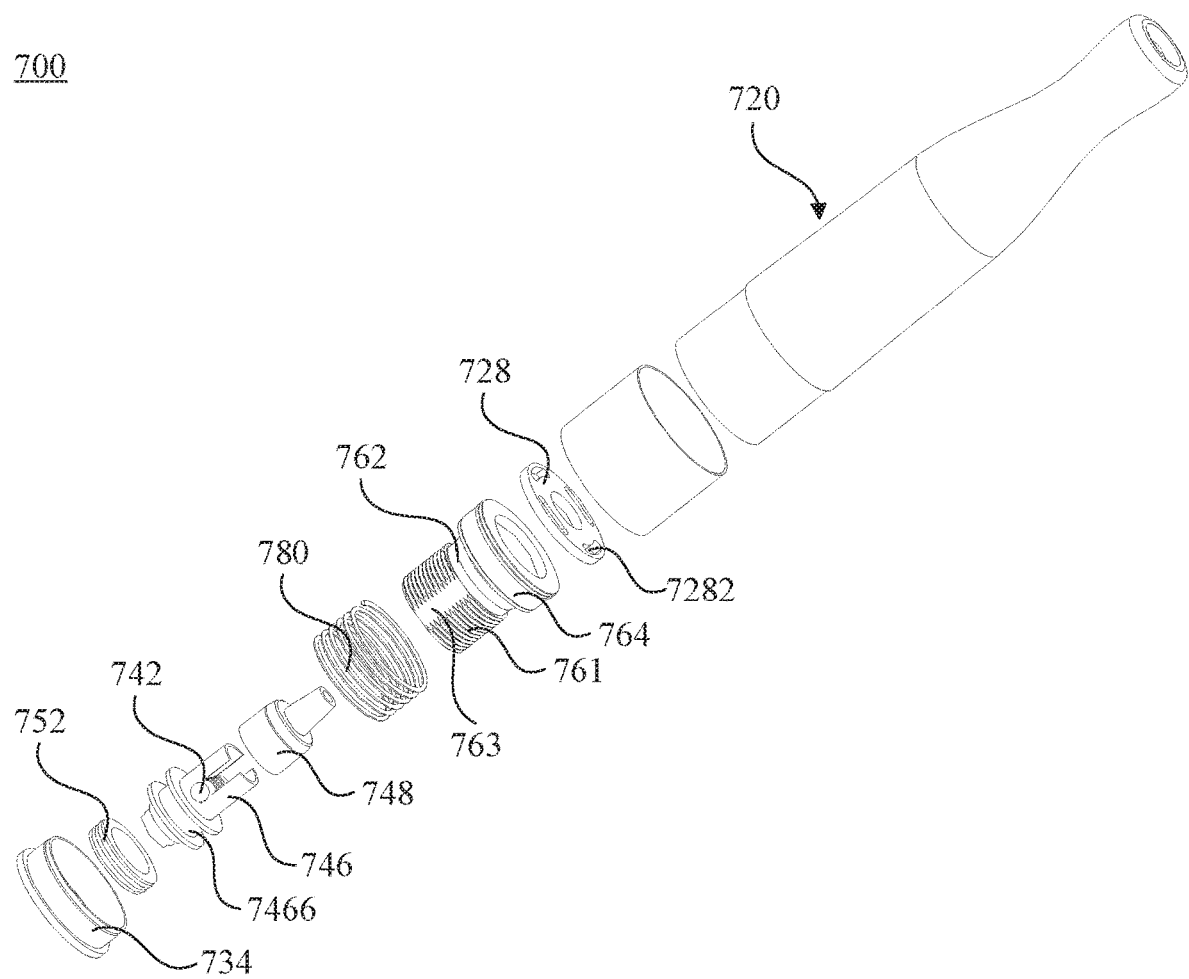
FIG. 9 is an exploded view of an atomizing assembly of the inhaler of FIG. 7.

Referring to FIG. 9, in one embodiment, the atomizing core 740 can further includes an atomizing base 746 and an atomizing cover 748. The atomizing base defines an atomizing chamber 7462 and a liquid absorbing opening. The wick 742 is at least partially located inside the atomizing chamber 7462. The wick 742 is in contact with the liquid in the auxiliary liquid storage chamber 723 via the liquid absorbing opening 7464. The atomizing cover 748 is located on the atomizing base 746. The atomizing cover 748 extends at least partially into an inside of the inner tube 724. The atomizing cover 748 defines a communication aperture communicating the atomizing chamber 7462 and the air flow channel 7242. The atomization cover 748 can be resilient to seal a gap between the inner tube 724 and the atomization core 740. Meanwhile, the atomization cover 748 can cushion the pressure applied to the inner tube 724 by the atomizing core 740 during the assembly of the battery assembly 900, thus increasing the reliability of the structure.

Figure 10:
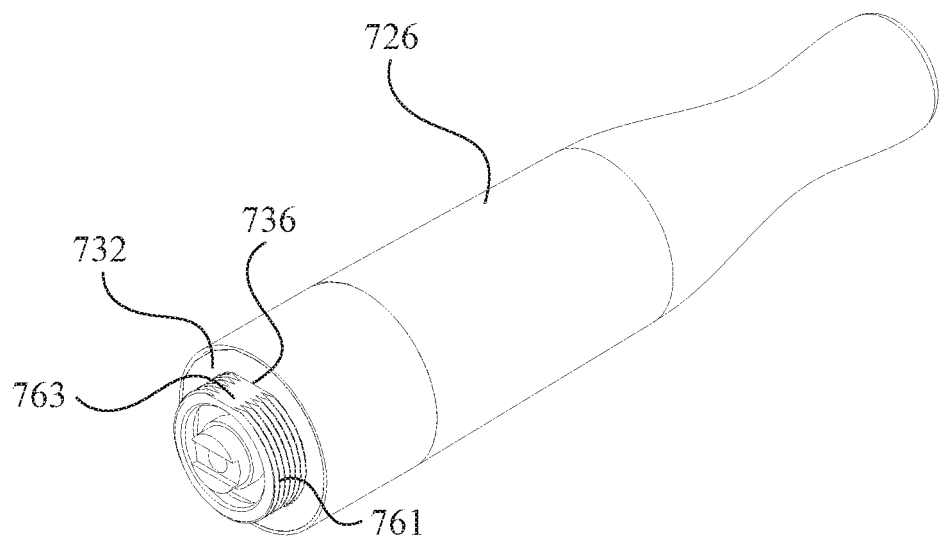
FIG. 10 is a perspective view of the atomizing assembly of the inhaler of FIG. 7.

Further, referring to FIG. 10, in the illustrated embodiment, the movable member 760 is provided with a first thread 761, the battery assembly 900 is provided with a second thread 940. The first thread 761 can be engaged with the second thread 940 on the battery assembly 900. The battery assembly 900 rotatably drives the movable member 760 to move, so as to open the liquid-draining aperture 7282.

In one embodiment, the atomization assembly 700 of the inhaler 70 further includes an elastic member 780. One end of the elastic member 780 is connected to the movable member 760, the other end of the elastic member 780 is connected to the liquid reservoir 720. A direction of force applied to the movable member 760 by the elastic member 780 is opposite to a moving direction of the movable member 760 when the movable member 760 moves towards the battery assembly 900.

When the atomization assembly 700 is assembled with the battery assembly 900, the battery assembly 900 is rotated to pull the movable member 760 towards the battery assembly 900, such that the liquid-draining aperture 7282 is opened. The elastic member 780 can be a spring, a rubber tube, a rubber pad, or a set of resilient sheet. In the illustrated embodiment, the elastic member 780 is a pressed spring. When the atomization assembly 700 is separated from the battery assembly 900, the elastic member 780 applies a reverse force to the movable member 760 to seal the liquid-draining aperture 7282.

In one embodiment, the movable member 760 includes a main body 762, and a sealing member 764. The main body 762 is shaped as a barrel and is movably sleeved on the atomizing base 746. The sealing member 764 is located at an end of the main body 762 proximately to the liquid guide piece 728, and the sealing member 764 is aligned with the liquid-draining aperture 7282. The sealing member 764 can be made of an elastic material such as silica gel. The configuration of the sealing member 764 can improve the sealing effect of the movable member 760 to the liquid-draining aperture 7282 when the atomization assembly 700 is not connected to the battery assembly 900. The sealing member 764 defines an embedding groove on an inner side thereof, and the main body 762 is provided with a protruding ring. The protruding ring is embedded in the embedding groove, such that the main body 762 is firmly connected to the sealing member 764. In one embodiment, the elastic member 780 is sleeved on the main body 762, and the end of the elastic member 780 abuts the sealing member 764. The first thread 761 is an external thread, and the second thread 940 is an internal thread. The first thread 761 is located at one end of the main body 762 proximately to the battery assembly 900.

Figure 11:
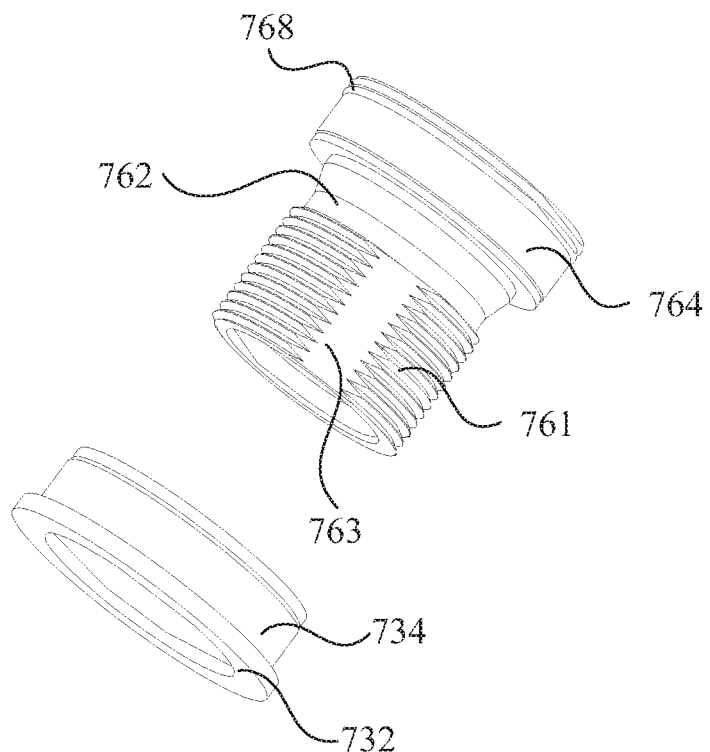
FIG. 11 is a schematic view of a main body and a stop ring of the inhaler of FIG. 7.

Referring to FIG. 11, the sealing member 764 is located inside the outer tube 726. The movable member 760 further includes a first sealing ring 768 disposed on the sealing member 764. The first sealing ring 768 is located between the sealing member 764 and the outer tube 726. When the movable member 760 moves along the inner wall of the outer tube 726, the first sealing ring 768 can prevent the liquid flowing from the liquid-draining aperture 7282 from penetrating into a cavity where the elastic member 780 is located, thus the liquid cannot be leaked to the outside through a gap between the movable member 760 and the liquid reservoir 720.

Referring to FIG. 9, further in one embodiment, the atomizing core 740 further includes a second sealing ring 752, the atomizing base 746 defines an annular groove 7466 on an outer wall thereof, the second sealing ring 752 is at least partially embedded in the annular groove 7466, thereby sealing a gap between the main body 762 and the atomizing base 746. When the movable member 760 moves towards the battery assembly 900 until the liquid-draining aperture 7282 is opened, the liquid can flow from the main liquid storage chamber 722 into the chamber where the wick is located. The second sealing ring can prevent leakage of the liquid in the chamber.

Figure 12:
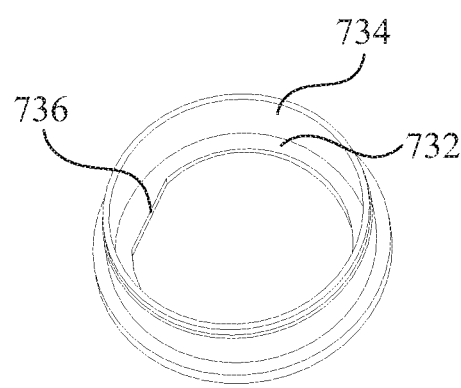
FIG. 12 is a schematic view of a positioning portion of the inhaler of FIG. 7.

Referring also to FIG. 12, in one embodiment, the liquid reservoir 720 further includes a support base 732 and a stop ring 734. The support base 732 has an annular shape and is located on an opening of the outer tube 726. The support base 732 is fixed to the outer tube 726. The main body 762 extends through the support base 732. The elastic member 780 has an end abutting the support base 732. The stop ring 734 is located between the outer tube 726 and the atomizing base 746. The stop ring 734 is fixed to the support base 732. In one embodiment, the stop ring 734 and the support base 732 can be integrally formed. The elastic member 780 is located between the stop ring 734 and the main body 762. When the elastic member 780 moves in a gap between the stop ring 734 and the main body 762, the movement of the elastic member 780 can be guided by the stop ring 734 and the main body 762. Meanwhile, the stop ring can restrict the movement of the movable member 760, so as to determine the distance by which the movable member 760 is moved when the battery assembly 900 is assembled.

In one embodiment, the liquid reservoir 720 further includes a positioning portion 736, which is located on the support base 732. The positioning portion 736 protrudes from an inner side of the support base 732. The sidewall of the main body 762 has a notch 763 extending in an axial direction of the main body 762. The positioning portion 736 engages with the notch 763 to prevent the movable member 760 from rotating with respect to the support base 732, thereby increasing the stability and the sealability.

Figure 13:
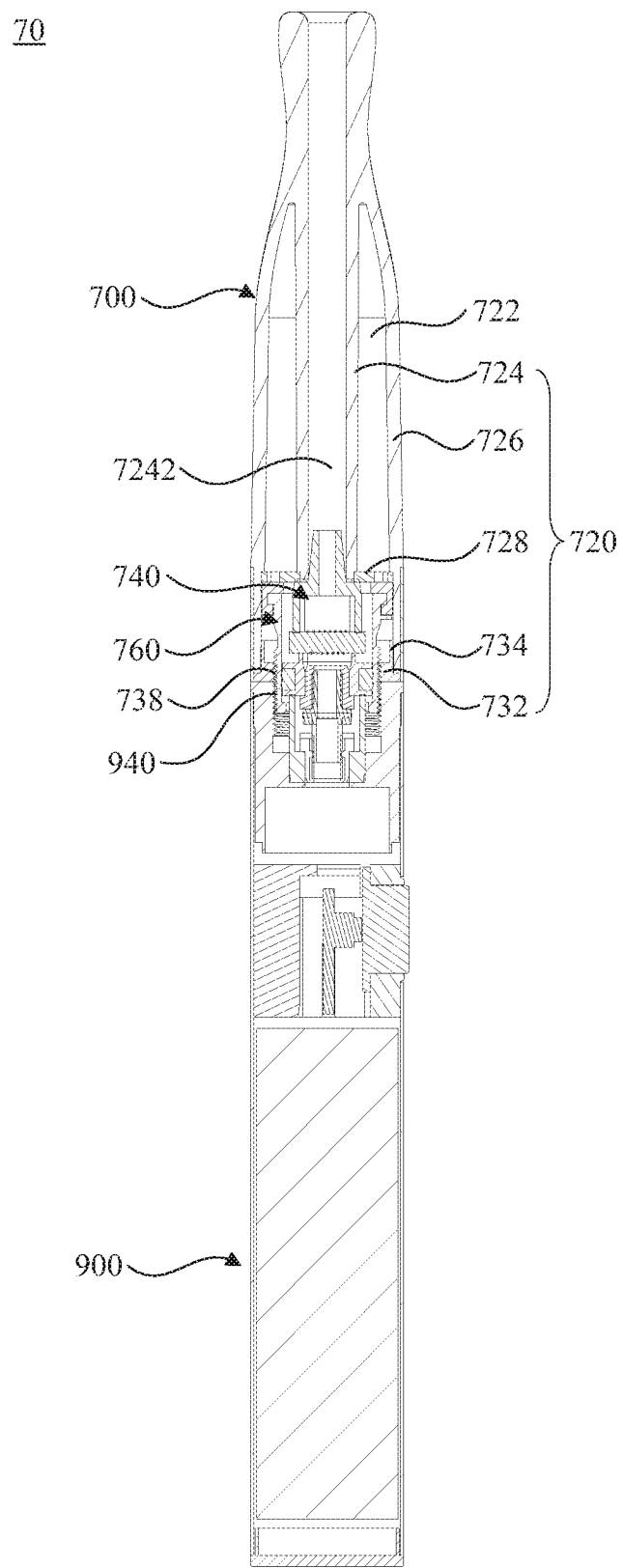
FIG. 13 is a cross-sectional view of an inhaler according to yet another embodiment.
Figure 14:
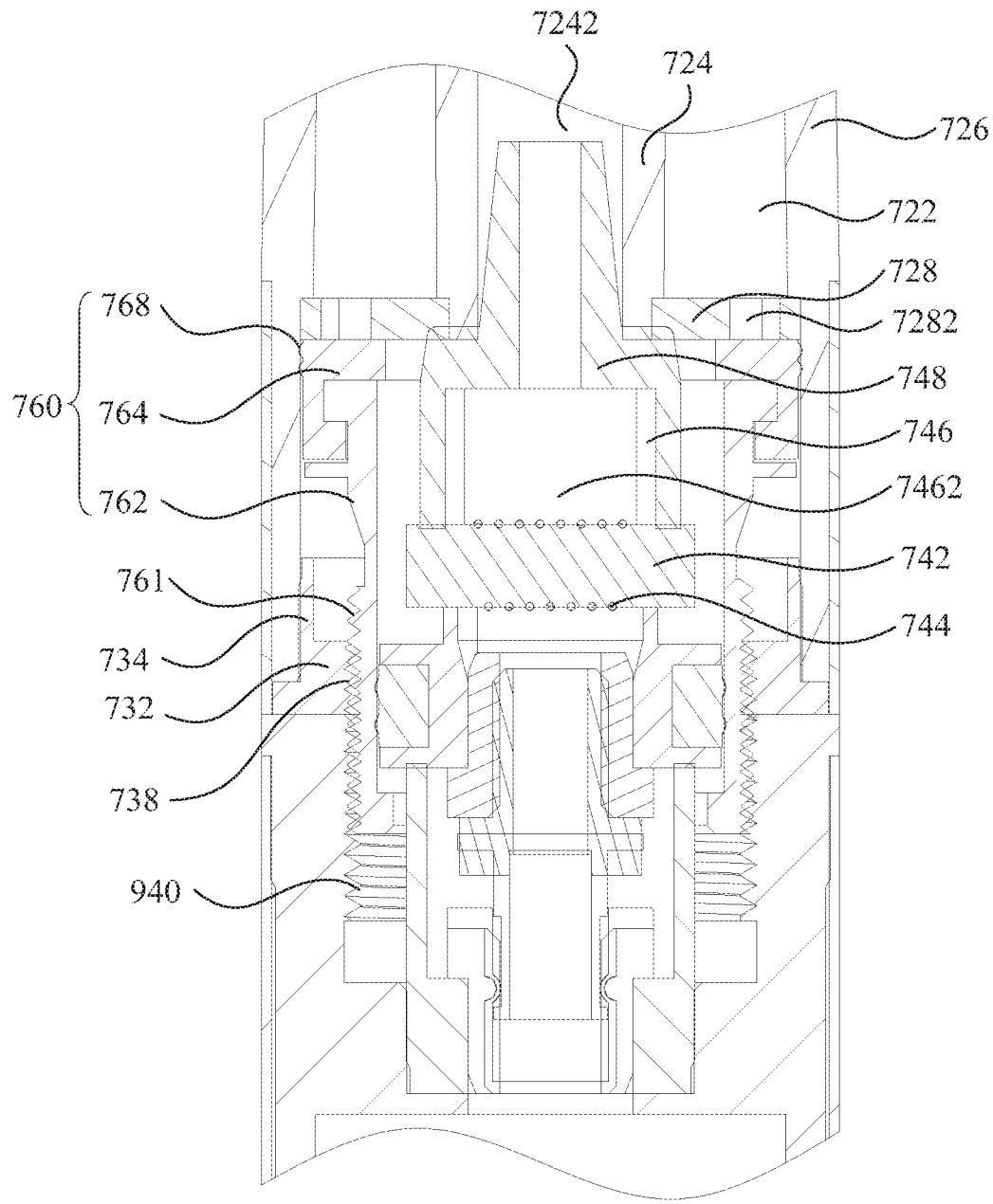
FIG. 14 is an enlarged view of the inhaler of FIG. 13.
Figure 15:
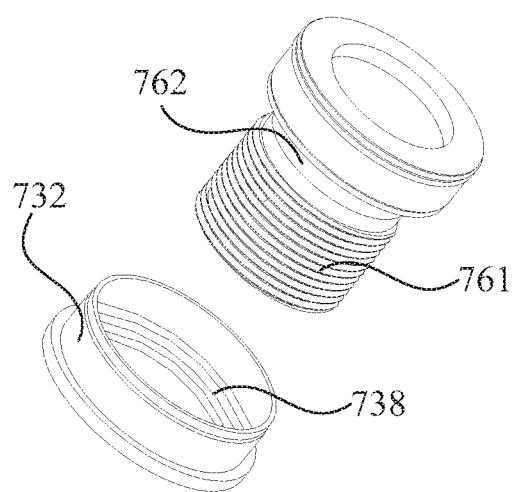
FIG. 15 is a schematic view of a first thread and a third thread of the inhaler of FIG. 13.

Of course, the battery assembly 900 can drive the movable member 760 to move in other manners, for example, in an alternative embodiment shown in FIGS. 13 to 15, the liquid reservoir 720 is provided with a third thread 738, which can be engaged with the first thread 761. The elastic member 780 can be omitted. When the atomization assembly 700 is not connected to the battery assembly 900, the third thread 738 can limit the movable member 760 to abut the liquid guide piece 728, thus sealing the liquid-draining aperture 7282. The third thread 738 can be provided on the support base 732.

Although the respective embodiments have been described one by one, it shall be appreciated that the respective embodiments will not be isolated. Those skilled in the art can apparently appreciate upon reading the disclosure of this application that the respective technical features involved in the respective embodiments can be combined arbitrarily between the respective embodiments as long as they have no collision with each other. Of course, the respective technical features mentioned in the same embodiment can also be combined arbitrarily as long as they have no collision with each other.

The foregoing descriptions are merely specific embodiments of the present invention, but are not intended to limit the protection scope of the present invention. Any variation or replacement readily figured out by a person skilled in the art within the technical scope disclosed in the present invention shall all fall within the protection scope of the present invention. Therefore, the protection scope of the present invention shall be subject to the protection scope of the appended claims.

What is claimed is:

1. An atomization assembly of an inhaler, comprising:
a liquid reservoir defining a main liquid storage chamber therein for storing liquid and an auxiliary liquid storage chamber, the liquid reservoir further defining a liquid-draining aperture between the main liquid storage chamber and the auxiliary liquid storage chamber, the liquid-draining aperture located at a bottom surface of the main liquid storage chamber;
an atomizing core fixed to the liquid reservoir; and
a movable member configured to move back and forth between a first position towards the liquid-draining aperture and a second position away from the liquid-draining aperture, wherein when the movable member is in the first position, the movable member seals the liquid-draining aperture, such that the main liquid storage chamber is isolated from the auxiliary liquid storage chamber; when the movable member is in the second position, the movable member is separated from the liquid-draining aperture, thereby communicating the main liquid storage chamber with the auxiliary liquid storage chamber;
wherein the atomization assembly is configured to be detachably connected to a battery assembly of the inhaler, when the atomization assembly is not connected to the battery assembly, the movable member seals the liquid-draining aperture; when the atomization assembly is connected to the battery assembly, the movable member moves towards the battery assembly and is separated from the liquid-draining aperture;
wherein the liquid reservoir comprises an inner tube, an outer tube, and a liquid guide piece, the inner tube defines an air flow channel therein, the main liquid storage chamber is formed between the inner tube and the outer tube, the liquid guide piece is located at an end of the inner tube and separates the main liquid storage chamber from the auxiliary liquid storage chamber, the liquid-draining aperture is defined on the liquid guide piece.

2. The atomization assembly according to claim 1, wherein the atomizing core is located in the auxiliary liquid storage chamber, the atomizing core comprises:
a wick;
an atomizing base defining an atomizing chamber and a liquid absorbing opening, the wick is at least partially located inside the atomizing chamber, the wick is in contact with the liquid in the liquid storage chamber via the liquid absorbing opening; and
an atomizing cover located on the atomizing base, the atomizing cover extends at least partially into an inside of the inner tube, and the atomizing cover defines a communication aperture communicating the atomizing chamber and the air flow channel.

3. The atomization assembly according to claim 1, wherein at least part of the movable member is made of a magnetic material, the movable member is capable of being attracted by a magnet in the battery assembly to move towards the battery assembly;
wherein the atomization assembly further comprises an elastic member, one end of the elastic member is connected to the movable member, the other end of the elastic member is connected to the liquid reservoir, a direction of urging the movable member by the elastic member is opposite to a moving direction of the movable member when the movable member moves towards the battery assembly.

4. The atomization assembly according to claim 3, wherein the movable member comprises:
a main body movably sleeved on the atomizing base;
a sealing member located at an end of the main body proximately to the liquid guide piece, the sealing member being aligned with the liquid-draining aperture; and
a ferric member located at an end of the main body proximately to the battery assembly.

5. The atomization assembly according to claim 1, wherein the movable member is provided with a first thread engaging with a second thread on the battery assembly, the battery assembly rotatably drives the movable member to move.

6. The atomization assembly according to claim 5, further comprising an elastic member, wherein one end of the elastic member is connected to the movable member, the other end of the elastic member is connected to the liquid reservoir, a direction of urging the movable member by the elastic member is opposite to a moving direction of the movable member when the movable member moves towards the battery assembly.

7. The atomization assembly according to claim 6, wherein the movable member comprises:
a main body shaped as a barrel, the main body being movably sleeved on the atomizing base;
a sealing member located at an end of the main body proximately to the liquid guide piece, the sealing member being aligned with the liquid-draining aperture;
wherein the first thread is an external thread located at one end of the main body proximately to the battery assembly.

8. The atomization assembly according to claim 7, wherein the sealing member is located inside the outer tube, the movable member further comprises a first sealing ring disposed on the sealing member, the first sealing ring is located between the sealing member and the outer tube.

9. The atomization assembly according to claim 7, wherein the atomizing core comprises a second sealing ring, the atomizing base defines an annular groove on an outer wall thereof, the second sealing ring is at least partially embedded in the annular groove, thereby sealing a gap between the main body and the atomizing base.

10. The atomization assembly according to claim 7, wherein the liquid reservoir further comprises:
a support base having an annular shape and located on an opening of the outer tube, wherein the main body extends through the support base, an end of the elastic member abuts the support base; and
a stop ring located between the outer tube and the atomizing base, wherein the stop ring is fixed to the support base, and the elastic member is located between the stop ring and the main body.

11. The atomization assembly according to claim 10, wherein the liquid reservoir further comprises a positioning portion located on the support base, the positioning portion protrudes from an inner side of the support base, the sidewall of the main body has a notch extending in an axial direction thereof, the positioning portion is engaged in the notch to restrict the main body from rotating.

12. The atomization assembly according to claim 5, wherein the liquid reservoir is provided with a third thread engaging with the first thread.

13. An inhaler comprising:
an atomization assembly comprising:
a liquid reservoir defining a main liquid storage chamber and an auxiliary liquid storage chamber therein for storing liquid, the liquid reservoir further defining a liquid-draining aperture between the main liquid storage chamber and the auxiliary liquid storage chamber, the liquid-draining aperture located at a bottom surface of the main liquid storage chamber;
an atomizing core fixed to the liquid reservoir;
a movable member movably connected to the liquid reservoir; and
a battery assembly detachably connected to atomization assembly, wherein when the battery assembly is not connected to the atomization assembly, the movable member seals the liquid-draining aperture, such that the main liquid storage chamber is isolated from the auxiliary liquid storage chamber;
when the battery assembly is connected to the atomization assembly, the movable member moves towards the battery assembly and is separated from the liquid-draining aperture, thereby communicating the main liquid storage chamber with the auxiliary liquid storage chamber;
wherein at least part of the movable member is made of a magnetic material, the battery assembly comprises a magnet, the movable member is capable of being attracted by the magnet to move towards the battery assembly;
wherein the atomization assembly further comprises an elastic member, one end of the elastic member is connected to the movable member, the other end of the elastic member is connected to the liquid reservoir, a direction of urging the movable member by the elastic member is opposite to a moving direction of the movable member when the movable member moves towards the battery assembly;
wherein the movable member comprises:
a main body movably sleeved on the atomizing base;
a sealing member located at an end of the main body proximately to the liquid guide piece, the sealing member being aligned with the liquid-draining aperture; and
a ferric member located at an end of the main body proximately to the battery assembly.

14. The inhaler according to claim 13, wherein the movable member is provided with a first thread engaging with a second thread on the battery assembly, the battery assembly rotatably drives the movable member to move.

15. The inhaler according to claim 14, wherein the atomization assembly further comprises an elastic member, one end of the elastic member is connected to the movable member, the other end of the elastic member is connected to the liquid reservoir, a direction of urging the movable member by the elastic member is opposite to a moving direction of the movable member when the movable member moves towards the battery assembly.

16. The inhaler according to claim 14, wherein the movable member comprises:
a main body shaped as a barrel, the main body being movably sleeved on the atomizing base;
a sealing member located at an end of the main body proximately to the liquid guide piece, the sealing member being aligned with the liquid-draining aperture;
wherein the first thread is an external thread located at one end of the main body proximately to the battery assembly.

17. An atomization assembly of an inhaler, comprising:
a liquid reservoir defining a main liquid storage chamber therein for storing liquid and an auxiliary liquid storage chamber, the liquid reservoir further defining a liquid-draining aperture between the main liquid storage chamber and the auxiliary liquid storage chamber, the liquid-draining aperture located at a bottom surface of the main liquid storage chamber;
an atomizing core fixed to the liquid reservoir; and
a movable member configured to move back and forth between a first position towards the liquid-draining aperture and a second position away from the liquid-draining aperture, wherein when the movable member is in the first position, the movable member seals the liquid-draining aperture, such that the main liquid storage chamber is isolated from the auxiliary liquid storage chamber; when the movable member is in the second position, the movable member is separated from the liquid-draining aperture, thereby communicating the main liquid storage chamber with the auxiliary liquid storage chamber;
wherein the atomization assembly is configured to be detachably connected to a battery assembly of the inhaler, when the atomization assembly is not connected to the battery assembly, the movable member seals the liquid-draining aperture; when the atomization assembly is connected to the battery assembly, the movable member moves towards the battery assembly and is separated from the liquid-draining aperture;
wherein at least part of the movable member is made of a magnetic material, the movable member is capable of being attracted by a magnet in the battery assembly to move towards the battery assembly;
wherein the atomization assembly further comprises an elastic member, one end of the elastic member is connected to the movable member, the other end of the elastic member is connected to the liquid reservoir, a direction of urging the movable member by the elastic member is opposite to a moving direction of the movable member when the movable member moves towards the battery assembly;
wherein the movable member comprises:
a main body movably sleeved on the atomizing base;
a sealing member located at an end of the main body proximately to the liquid guide piece, the sealing member being aligned with the liquid-draining aperture; and
a ferric member located at an end of the main body proximately to the battery assembly.

* * * * *